United States Patent [19]

Jujo

[11] Patent Number: 4,912,261

[45] Date of Patent: Mar. 27, 1990

[54] STABLE ISOPROPENYL ACETOPHENONE SOLUTIONS

[75] Inventor: Yozo Jujo, Tokyo, Japan

[73] Assignee: Mitsui Petrochemical Industries, Ltd., Tokyo, Japan

[21] Appl. No.: 265,780

[22] Filed: Nov. 1, 1988

[51] Int. Cl.[4] .............................................. C07C 45/86
[52] U.S. Cl. .................................................... 568/304
[58] Field of Search ............................... 568/304, 373; 252/182.18, 407

[56] References Cited

U.S. PATENT DOCUMENTS 2,105,284  1/1938  Groll et al. ............................ 568/304
2,210,838  8/1940  Lange et al. .......................... 568/304

FOREIGN PATENT DOCUMENTS 48-72110   9/1973  Japan ..................................... 568/304
1046239   10/1983  U.S.S.R. ................................ 568/304

Primary Examiner—James H. Reamer
Attorney, Agent, or Firm—Sherman and Shalloway

[57] ABSTRACT

In accordance with the present invention, there are obtained stable isopropenyl acetophenone solutions containing (i) an organic carboxylic acid and/or (ii) a specific diluent and, if necessary, (iii) a radical polymerization inhibitor. Because of such composition as mentioned above, the present isopropenyl acetophenone solutions are quite useful and excellent in stability, especially long-term preservation performance, showing practically no polymerization of the isopropenyl acetophenone contained therein even when the solutions are preserved for an extended period of time under the circumstances of high temperature.

6 Claims, No Drawings

| # STABLE ISOPROPENYL ACETOPHENONE SOLUTIONS

FIELD OF THE INVENTION

This invention relates to stable isopropenyl acetophenone solutions and more particularly to stable solutions containing isopropenyl acetophenone which is useful as a starting material for the preparation of polyester resins, polycarbonate resins, polyurethane resins and the like which are excellent in heat resistance and mechanical strength.

BACKGROUND OF THE INVENTION

It is known that isopropenyl acetophenone is a compound useful as a starting material for the preparation of polyester resins, polycarbonate resins, polyurethane resins and the like which are excellent in physical properties, particularly heat resistance and mechanical strength, or as an additive for macromolecular materials or as a starting material for agricultural chemicals or pharmaceutical preparations.

For instance, triphenol type compounds can be obtained by the reaction of isopropenyl acetophenone with phenols, and the triphenol type compounds obtained are used at the time when polycarbonate resins are prepared.

However, isopropenyl acetophenone polymerizes to a certain extent when it is allowed to stand at room temperature, and it is extremely liable to polymerize when stored under the circumstances of high temperature. Because of its high polymerizability as mentioned above, isopropenyl acetophenone had such problems that a loss of isopropenyl acetophenone is incurred during storage thereof, or when other compounds are intended to be prepared by the use of isopropenyl acetophenone which has partially polymerized during storage thereof, the compounds obtained thereby come to deteriorate in quality.

Since isopropenyl acetophenone is liable to polymerize and difficult to store in the manner now described, utilization of isopropenyl acetophenone is markedly limited in present circumstances.

We conducted extensive researches with the view of obtaining stable isopropenyl acetophenone solutions which are capable of preserving the isopropenyl acetophenone contained therein for an extended period of time without causing polymerization thereof, and have eventually accomplished the present invention on the basis of our finding that isopropenyl acetophenone solutions containing specific compounds in combination with the isopropenyl acetophenone are quite stable.

OBJECT OF THE INVENTION

The present invention is intended to solve such problems associated with the prior art as mentioned above, and an object of the invention is to provide stable isopropenyl acetophenone solutions which will not bring about polymerization of the isopropenyl acetophenone contained therein even when said solutions are stored for an extended period of time.

SUMMARY OF THE INVENTION

The first stable isopropenyl acetophenone solution of the present invention is characterized by containing
(i) 5–10,000 ppm of an organic carboxylic acid and/or
(ii) 5–2,000 parts by weight, based on 100 parts by weight of isopropenyl acetophenone of at least one diluent selected from the group consisting of aromatic hydrocarbons, aliphatic hydrocarbons and phenols.

Further, the second stable isopropenyl acetophenone solution of the present invention is characterized by containing
(i) 5–10,000 ppm of an organic carboxylic acid and/or
(ii) 5–2000 parts by weight, based on 100 parts by weight of isopropenyl acetophenone of at least one diluent selected from the group consisting of aromatic hydrocarbons, aliphatic hydrocarbons and phenols, and
(iii) 5–10,000 ppm of a radical polymerization inhibitor.

The stable isopropenyl acetophenone solutions of the present invention contain (i) an organic carboxylic acid and/or (ii) a specific diluent and, if necessary, (iii) a radical polymerization inhibitor, and hence practically no isopropenyl acetophenone contained therein will polymerize even when the solutions are stored for an extended period of time, thus the present isopropenyl acetophenone solutions are excellent in stability.

DETAILED DESCRIPTION OF THE INVENTION

The stable isopropenyl acetophenone solutions of the present invention are illustrated below in detail.

As mentioned previously, the stable isopropenyl acetophenone solutions of the present invention contain (i) an organic carboxylic acid and/or (ii) a diluent and, if necessary, (iii) a radical polymerization inhibitor. Then, these components contained in the solutions are illustrated hereinafter.

(i) Organic carboxylic acid

By virtue of the incorporation into isopropenyl acetophenone solutions of an aliphatic carboxylic acid having at least one hydroxyl group, there are provided stable isopropenyl acetophenone solutions in which polymerization of the isopropenyl acetophenone contained is inhibited.

Organic carboxylic acids useful for the purpose intended are citric acid, tartaric acid, ascorbic acid, gluconic acid, and the like.

The organic carboxylic acid as mentioned above is incorporated into the isopropenyl acetophenone solution in an amount of 5–10,000 ppm, preferably 50–8,000 ppm and more preferably 50–2,000 ppm. The incorporation into the solution of the organic carboxylic acid in an amount less than 5 ppm is undesirable, because polymerization of the isopropenyl acetophenone in said solution cannot be effectively inhibited and, on the other hand, the incorporation of the organic carboxylic acid in an amount in excess of 10,000 ppm is also undesirable, because the excess organic carboxylic acid present in the solution becomes an inhibitory substance when the isopropenyl acetophenone contained in said solution is intended for use as a starting material for the synthesis of other compounds.

(ii) Diluent

By virtue of the incorporation into isopropenyl acetophenone solutions of a diluent, there are obtained likewise stable isopropenyl acetophenone solutions in which polymerization of the isopropenyl acetophenone is inhibited.

Useful diluents for the purpose intended are at least one compound selected from the group consisting of aromatic hydrocarbons, aliphatic hydrocarbons and phenols.

Useful aromatic hydrocarbons include alkylbenzenes such as toluene, xylene, benzene, mesitylene, etc., halogenated aromatic hydrocarbons such as chlorobenzene, bromobenzene, etc., and nitrogen containing aromatic hydrocarbons such as aniline, etc.

Useful aliphatic hydrocarbons include straight chain or branched aliphatic hydrocarbons such as n-decane, hexane, etc., cycloaliphatic hydrocarbons such as cyclohexane, etc. and alcohols.

Useful phenols include monovalent phenols such as phenol, cresol, etc., and divalent phenols such as hydroquinone, bisphenol A, etc.

Such diluents are mentioned above are used in the isopropenyl acetophenone solutions of the present invention is an amount of 5–2,000 parts by weight, preferably 10–500 parts by weight, based on 100 parts by weight of isopropenyl acetophenone. The use of the diluent amounting to less than 5 parts by weight is undesirable, because polymerization of the isopropenyl acetophenone contained in the solution cannot be inhibited effectively and, on the other hand, the use of the diluent is an amount exceeding 2,000 parts by weight is undesirable, because not only does the solution become undesirably bulky for storage as well as transportation thereof but also a step of scavenging the diluent once used becomes necessary under certain circumstances.

(iii) Radical polymerization inhibitor

In the present invention, the isopropenyl acetophenone solutions are incorporated, if necessary, with (iii) a radical polymerization inhibitor in addition to (i) an organic carboxylic acid and (ii) a diluent as mentioned previously.

Useful radical polymerization inhibitors for the purpose intended include t-butyl catechol, butyrated hydroxyanisole, quinones, nitro compounds, sulfur type antioxidants, phosphorus type antioxidants, etc.

Such radical polymerization inhibitors as mentioned above are incorporated into the isopropenyl acetophenone solutions in an amount of 5–10,000 ppm, preferably 50–8,000 ppm and more preferably 50–2,000 ppm.

It is noted in this connection, with great surprise, that in the present invention, polymerization is isopropenyl acetophenone cannot be inhibited even when the radical polymerization inhibitor is solely incorporated into the isopropenyl acetophenone solution in such an amount as defined above. This means that the polymerization is isopropenyl acetophenone is not a simple radical polymerization.

EFFECT OF THE INVENTION

Because the stable isopropenyl acetophenone solutions of the present invention contain (i) an organic carboxylic acid and/or (ii) a specific diluent and, if necessary, (iii) a radical polymerization inhibitor, the isopropenyl acetophenone contained therein will not practically polymerize even when the solutions are preserved for an extended period of time, thus the present isopropenyl acetophenone solutions are quite excellent in stability.

The present invention is illustrated below with reference to examples, but it should be construed that the invention is in no way limited to those examples.

EXAMPLE 1

Into a 50 ml three neck flask were charged 20 g of purified isopropenyl acetophenone and 1,000 ppm of citric acid as a diluent, and the mixture was heated in a nitrogen atmosphere at 80° C. On the 50th and 100th hour after heating, the amount by weight percent of the isopropenyl acetophenone in the flask was measured by GC internal indication method to obtain a percentage of retention (%) of isopropenyl acetophenone.

The percentages of retention as measured on the 50th hours and the 100th hours after heating were 92% and 86%, respectively.

EXAMPLES 2–14 AND COMPARATIVE EXAMPLES 1–2

The same experiment as in Example 1 was repeated except that the kind and amount of the polymerization inhibitor and of the diluent used in each of the present examples and in each of the comparative examples were changed in the manner as shown in Table 1, and the percentage of retention of isopropenyl acetophenone was measured in each case in the same manner as in Example 1.

The results obtained are shown in Table 1, including also the results obtained in Example 1.

TABLE 1

| | | Polymerization inhibitory effect on isopropenyl acetophenone at 80° C. | | | | | | |
|---|---|---|---|---|---|---|---|---|
| | | Organic carboxylic acid | | Diluent | | Radical polymerization inhibitor | | Change on standing |
| | | | | | (parts by weight based on 100 parts by weight of isopropenyl acetophenone) | | | 50 hours after Retention (%) | 100 hours after Retention (%) |
| | | Compound | Amount added (ppm) | Compound | | Compound | Amount added (ppm) | | |
| Example | 1 | Citric acid | 1000 | — | | — | | 92 | 86 |
| | 2 | Tartaric acid | 1000 | — | | — | | 92 | 86 |
| | 3 | Tartaric acid | 400 | — | | — | | 91 | 85 |
| | 4 | Tartaric acid | 100 | — | | — | | 91 | 85 |
| | 5 | — | | Toulene | 100 | — | | 92 | 90 |
| | 6 | — | | n-Decane | 100 | — | | 92 | 91 |
| | 7 | — | | Phenol | 100 | — | | 95 | 92 |
| | 8 | — | | Phenol | 20 | — | | 93 | 88 |
| | 9 | Tartaric acid | 100 | Phenol | 100 | — | | 95 | 92 |
| | 10 | Citric acid | 100 | Toulene | 100 | — | | 93 | 90 |
| | 11 | Tartaric acid | 100 | | | TBC | 100 | 98 | 97 |
| | 12 | Tartaric acid | 100 | | | 4-Methoxyphenol | 100 | 97 | 96 |
| | 13 | Tartaric acid | 100 | Phenol | 100 | TBC | 100 | 100 | 99 |
| | 14 | Tartaric acid | 50 | Toulene | 50 | TBC | 50 | 99 | 98 |
| Compar. | | | | | | | | | |

TABLE 1-continued

| | Polymerization inhibitory effect on isopropenyl acetophenone at 80° C. | | | | | | |
|---|---|---|---|---|---|---|---|
| | Organic carboxylic acid | | Diluent (parts by weight based on 100 parts by weight of isopropenyl acetophenone) | | Radical polymerization inhibitor | | Change on standing |
| | Compound | Amount added (ppm) | Compound | | Compound | Amount added (ppm) | 50 hours after Retention (%) | 100 hours after Retention (%) |
| Example 1 | — | | | | — | | 90 | 84 |
| 2 | — | | | | TBC | 100 | 91 | 84 |

What is claimed is:

1. A stable isopropenyl acetophenone solution comprising
   (i) 5–10,000 ppm of an aliphatic carboxylic acid having at least one hydroxyl group, and
   (ii) 5–2,000 parts by weight, based on 100 parts by weight of isopropenyl acetophenone, of at least one diluent selected from the group consisting of aromatic hydrocarbons, aliphatic hydrocarbons and phenols.

2. The stable isopropenyl acetophenone solution as claimed in claim 1 wherein the aliphatic carboxylic acid having at least one hydroxyl group is citric acid, tartaric acid, ascorbic acid or gluconic acid.

3. The stable isopropenyl acetophenone solution as claimed in claim 1 wherein the diluent is toluene, xylene, benzene, mesitylene, n-decane, hexane, phenol, cresol, hydroquinone or bisphenol A.

4. A stable isopropenyl acetophenone solution comprising
   (i) 5–10,000 ppm of an aliphatic carboxylic acid having at least one hydroxyl group, and/or
   (ii) 5–2,000 parts by weight, based on 100 parts by weight of isopropenyl acetophenone, of at least one diluent selected from the group consisting of aromatic hydrocarbons, aliphatic hydrocarbons and phenols, and
   (iii) 5–10,000 ppm of a radical polymerization inhibitor selected from the group consisting of t-butyl catechol, 4-methoxy phenol, butyrated hydroxyanisole, quinones, nitro compounds, sulfur type antioxidants and phosphorous type antioxidants.

5. The stable isopropenyl acetophenone solution as claimed in claim 4 wherein the aliphatic carboxylic acid having at least one hydroxyl group is citric acid, tartaric acid, ascorbic acid or gluconic acid.

6. The stable isopropenyl acetophenone solution as claimed in claim 4 wherein the diluent is toluene, xylene, benzene, mesitylene, n-decane, hexane, phenol, cresol, hydroquinone or bisphenol A.

* * * * *